United States Patent [19]
Ohlsson et al.

[11] Patent Number: 5,915,965
[45] Date of Patent: Jun. 29, 1999

[54] DENTAL DEVICE AND THE WORKING TOOL TO BE EXCHANGED

[75] Inventors: Anders L. Ohlsson; Anders A. Stormats; H. Goran Svanberg, all of Nynashamn, Sweden

[73] Assignee: Amdent AB, Nynashamn, Sweden

[21] Appl. No.: 08/885,871

[22] Filed: Jun. 30, 1997

[30] Foreign Application Priority Data

Jan. 28, 1994 [SE] Sweden .................................. 9400328

[51] Int. Cl.[6] ........................................................ A61C 1/07
[52] U.S. Cl. ............................................ 433/118; 433/127
[58] Field of Search .............................. 433/86, 118, 119, 433/120, 121, 122, 123, 124, 127

[56] References Cited

U.S. PATENT DOCUMENTS

| 443,691 | 12/1890 | West ......................................... 433/121 |
| 3,286,558 | 11/1966 | Hufnagel ................................. 433/118 |
| 3,721,006 | 3/1973 | Malmin .................................... 433/141 |
| 3,930,173 | 12/1975 | Banko ...................................... 433/119 |
| 4,728,290 | 3/1988 | Eisner et al. ............................. 433/116 |
| 5,382,162 | 1/1995 | Sharp ....................................... 433/116 |

*Primary Examiner*—John J. Wilson
*Attorney, Agent, or Firm*—Larson & Taylor

[57] ABSTRACT

The invention relates to a dental device, and a method for exchanging a working tool at a dental device having an exchangeable vibrating of rotating working tool. The working tool (1,3,33) is corrected to a protective housing (2) to be mounted around a movement generating or transmitting device (5,5A). The working tool is exchangeable by aid of a turning operation of said housing (2) in relation of the movement generating or transmitting device.

11 Claims, 3 Drawing Sheets

DENTAL DEVICE AND THE WORKING TOOL TO BE EXCHANGED

Priority is hereby claimed under 35 U.S.C. § 120 based upon copending U.S. patent application Ser. No. 08/669,423, filed Jul. 9, 1996, now abandoned.

This invention relates to a dental device and an exchangeable working tool means for a dental device having a vibrating, oscillating working tool. The invention relates particularly to an improvement of a dental device having an ultra sonic vibrating dental tip, for instance a scalar, for removing teeth coatings.

BACKGROUND OF THE INVENTION

The Amdent Piezo Ultrasonic scalar device, comprises a core device having an oscillation generating part, which can not be sterilised and which is surrounded by an exchangeable, sterilisable, elongated protective housing functioning as a handle. The protective housing is open at its rear end and has an opening having a smaller diameter at its front end. This housing is mountable around the core device sealed with an 0-ring at its rear end towards an unloading socket and at its front end with an O-ring provided around the front of the core device. A scalar tip fixed to or integral with a nipple can be screwed onto the oscillation generating part through an opening at the front end of the sterilised housing first after that the housing has been mounted around the core device. The sterile scalar tip is then surrounded by a particular tip holder during the screwing operation in order to keep the sterilised tip sterile and to protect the operator from being injured by the tip. Thus, in this construction, the housing is not in thorough contact with the vibrating tip or a part of it.

SUMMARY OF THE INVENTION

The object of the invention is to provide a dental device in which the use of the particular tip holder is eliminated and which has an easy exchange of protective housing and working tip.

Yet another object is to provide a dental device having a housing and a tip held together when not mounted on a core device of a dental device.

Another object of the invention is to provide a dental device having a vibrating, oscillating tool with a non-vibrating handle.

At least some of these objects are achieved with a dental device having an exchangeable vibrating working tool, said working tool being connectable to a movement generating device around which a protective housing is mountable, comprising connecting means to connect said working tool to said protective housing, and means to transfer a rotating movement from said protective housing to said working tool.

According to the invention the tip and the handle are exchanged at the same time. This means that it is possible to operate the handle instead of a separate tip holder during the exchange of the tip. The holder and the tip are then kept together in one unit. It is to be noted that it is recommendable to have both a sterilised handle and a sterilised tip for each patient. In this way a particular tip holder is eliminated.

The use for the dental device according to the invention is not limited to scalar devices or the like but can be used for other kinds of dental devices having exchangeable vibrating working tools, for example rotating tools connectable to a movement generating or transferring unit.

BRIEF DESCRIPTION OF THE DRAWINGS

For a more complete understanding of the present invention and for further objects and advantages thereof, reference is now made to the following description taken in conjunction with the accompanying drawings, in which:

FIG. 2A shows a section, in larger scale than in FIG. 2A, of the front end of the housing in FIG. 2A provided on the core part.

DETAILED DESCRIPTION OF THE ILLUSTRATIVE EMBODIMENTS

Figure 1:
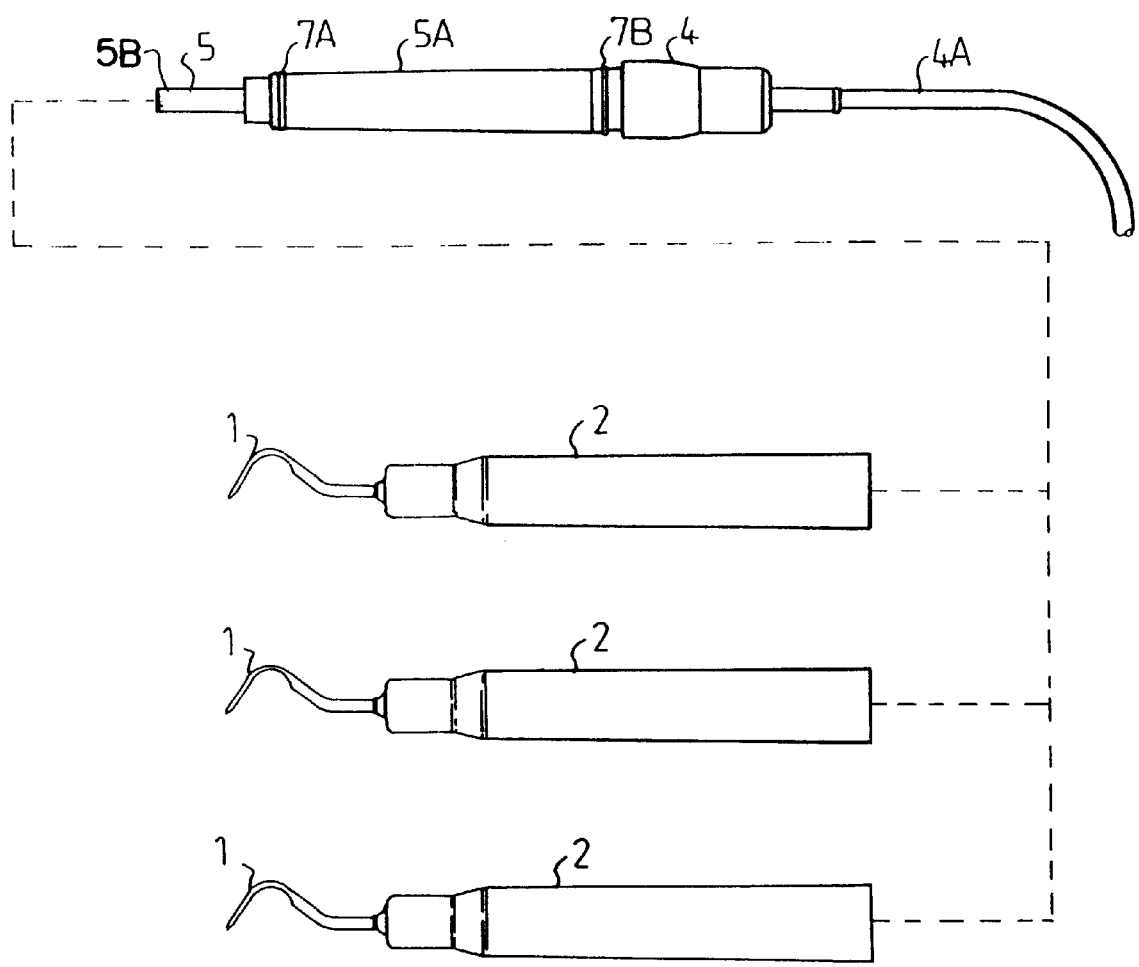
FIG. 1 shows a side view of an embodiment of a dental device having a vibration core part together with some exchangeable housings according to the invention.

Referring to FIG. 1, a dental device comprises a core part 5A having a vibrating part 53, comprising a protruding front tube part having an internal thread. A discharging sleeve 4 is provided at the rear end of the vibrating part 5. The core part 5A with the vibrating part 5 is connected to a conduit 4A for electric supply and supply of fluid through the sleeve 4. A couple of O-rings 7A and 7B are provided around the cure part 5A near the front end and rear end, respectively. Three protecting housings 2 can be mounted around the core part and will be held on place by the O-rings. The O-rings 7A and 7B have such thickness as to hold the housing 2 a distance from the core part 5A and is made by a rather soft material in order to suppress vibration transfer to the handle to a minimum. This is according to known technics.

Figure 2A:
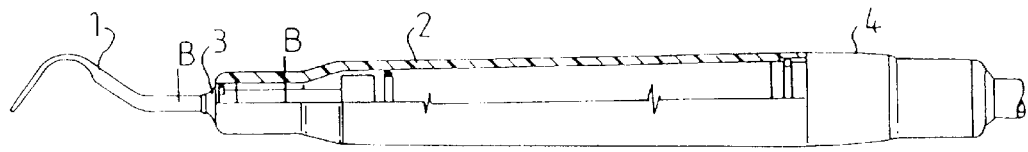
FIG. 2A shows a side view, partly in section, of a first embodiment of the housing provided on the core part, in accordance with the invention.
Figure 2B:
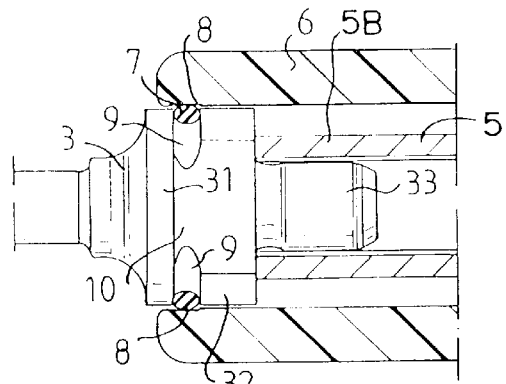
FIG. 2C shows a front end view of the housing in FIG. 2A without a connected tip.
Figure 2C:
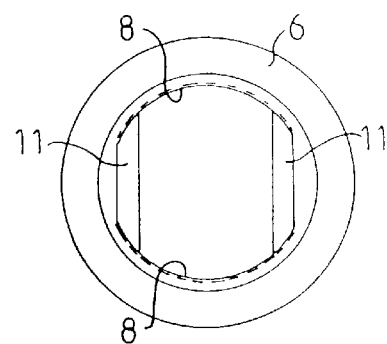
Figure 3A:
FIG. 3A shows a view from above of the device in FIG. 2A.
Figure 3B:
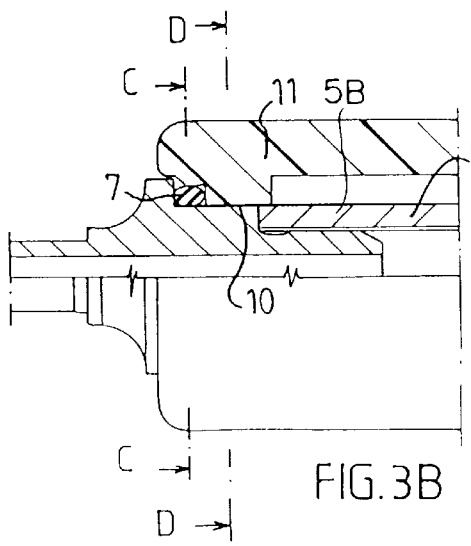
FIG. 3B shows a section along B—B in FIG. 3A in larger scale.
Figure 3C:
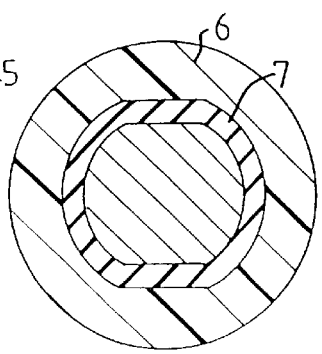
FIG. 3C shows a section along C—C in FIG. 3B.
Figure 3D:
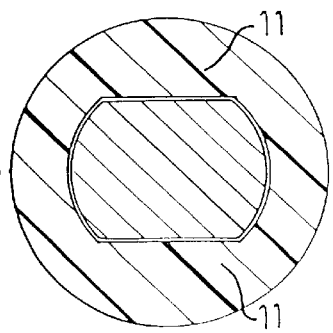
FIG. 3D shows a section along D—D in FIG. 3B.

According to the invention, the tip 1 is connected to the front end of the housing before the housing is provided on the core part. As apparent from FIGS. 2B and 3B, the tip 1 is fixed to, preferably integral with a nipple 3. Thus, in the embodiment shown, the nipple 3 flares to a circular flange 31 having a diameter slightly less than the inner diameter at the uttermost front end of a front part 6 of the protective housing 2. The nipple 3 is provided with a peripheral groove 9, just rear of its circular flange 31. A groove 8 is provided in the inner surface of the front side of the housing. An O-ring 7 of a soft material is provided in the groove 9 protruding somewhat from the surface of the nipple and adapted to rest into the groove 8 in the housing.

The O-ring 7 functions to hold together the protective housing and the nipple 3 in a releasable way when the housing/nipple/tip combination is not mounted on the core part and also functions as a vibration damping connection between the vibrating nipple 3 with the tip 1 and the housing. Also, the O-ring 7 seals the inside of the protective housing from intrusion of liquids and/or pollution.

The tip 1 shall be connected to the vibrating front tube part 5B which has an internal thread. The nipple 3 of the tip 1 has a threaded screw 33 at its rear part adapted to be screwed into the tube part 5B.

According to the invention the protective housing together with the tip is connectable to be secured on the core part by turning the protective housing 2 and holding the sleeve 4 stationary. Therefore, the contact between the nipple 3 of the tip 1 and the protective housing 2 is made not by a circular sectional form but by an non-circular sectional form providing work drive elements adapted to drive the tip around when rotating the housing 2. so that the screw 33 is screwed into the tube part 5B when the operator turns the handle.

In the embodiment shown in the Figures, the part of the nipple further inside the housing 2 is thus provided with a cut-off part 10 on two diametrical sides. The inner side 6 of the front end of the housing 2 is in turn provided with an inner profile adapted to the outer profile at 32,10 of the nipple 3 with its cut-off parts 10 and is thus provided with shoulders 11 functioning to draw the nipple 3 around while leaning against the cut-offs 10 when the housing is turned.

There is a little play between the outer profile 32,10 of the nipple and the part 6 with the shoulders 11 of the housing. At the turning operation the O-ring 7 is somewhat deformed in its peripheral direction and springs back to its normal condition as soon as the turning operation is finished. In this way transfer to the housing 2 of the vibration from the nipple with the tip 1 is avoided during work with the instrument on a patient's tooth.

Thus, the tip 1 can be provided on the vibrating core part together with the housing 2 without the need to touch the tip or to have a particular tip holder. The housing can be sterilised together with the tip and the tip and the housing need not be taken apart.

For example, the O-ring 7 may be exchanged by some other element or elements having the same functions, such as having the inside of the front part of the housing made of a soft elastic vibration damping and sealing material. Vibration damping material may be provided everywhere where surfaces between the tip/nipple and the housing meet.

The work drive arrangement between the nipple 3 and the inside of the housing can be designed in another way as the one shown, for instance having a hexagon structure, being provided with pins to be resting in grooves, or the like. The essential here is that the there is some kind of clamp tie function between the housing 2 and the tip device, and this means that is within the scope of the invention to have some kind of adapter between the two (not shown). Such kind of adapter may be useful in order to adapt invention for using tips on the market not having a form of its nipple exactly adapted to the inner form of the housing or being adaptable by some kind of simple cutting operation of its outer surface.

The connection between the nipple 3 and the vibrating part 5 can be provided in another way, for instance being in the form of a bayonet joint.

Figure 4A:
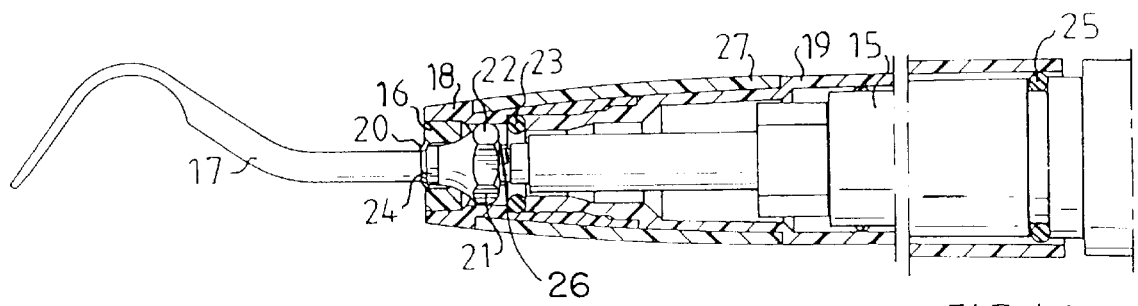
FIG. 4A shows a section through a second embodiment of the housing according to the invention just before the housing with its tip is attached to the core.
Figure 4B:
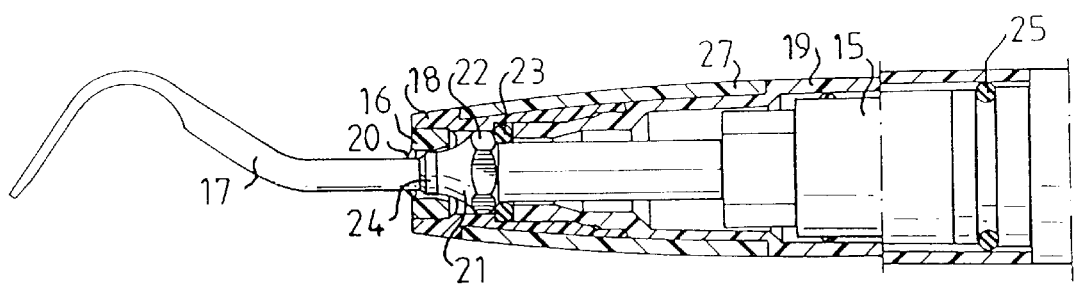
FIG. 4B shows the same section as FIG. 4A but when the housing with its tip is attached to the core.

In the embodiment shown in FIGS. 4A and 4B the sealing of the inside of the protective housing 19 and the centring of the housing around the core part 15 are divided to be performed essentially by two kinds of elements. This embodiment is the preferred one.

The sealing is provided by a ring 16 loosely provided on the nipple 21 of the working tool 17, for instance a scalar tip. The ring 16 has an outside diameter making a form sealing against an inner wall of the uttermost front end 18 of the protective housing 19. Both the inner wall and the outside of the ring 16 are slightly conical having the smaller diameter at the front end in order to provide a firm grip between them to keep the working tool 17 on place as soon as it is seated in the protective housing 19 even though the working tool has not been fixed on the core part 15, for instance by being screwed into it.

Thus, when mounting the working tool in the protective housing the nipple part of the tool is inserted in the front part 18 of the protective housing 19, whereupon the ring 16 is pressed into the front end of the housing. The unit working tool/protective housing could then be sterilised together before use.

The ring has preferably an inner lip 20 at its front part sealingly mounted around the base of the working tool near to its nipple part 21. As apparent from FIG. 4A, the ring 16 has an inside form adapted to the conically flaring outside form of the nipple part 21, particularly when the rear threaded part 26 of the tool 17 is not screwed into the core part 15. However, the working tool is provided with a ringformed projection 24 sealingly gliding along the inside of the ring 16 at mounting and demounting of the protective housing 19 with the tip on the core part. When it is screwed in, as shown in FIG. 4B, the inner part 22 of the nipple part 21 of the working tool is pressed against a ring 23 here making an extra seal. By this kind of constructive feature water or other fluids are prevented from intrude into the sensitive core part 15, not even when it is mounted on the core part and handled by the operator but also when the protective housing with the working tool is demounted from the core part.

The centering feature is provided by the ring 23 seated in the protective housing, in a groove inside it, near its front part and a ring 25 seated at the rear end of the core part 15. The core part 15 and the protective housing 19 are slightly conical at least at this rear end and the centering is thus made conically when the working tool 17 is screwed into the core part 15.

As the non-circular section of mating parts of the outside of a part of said working tool, such as the scalar tip, the inner part 22 of the tool has a symmetrical outer form resembling the form of a barrel nut and the inside of the front part 18 of protective housing 19 at the section where the part 22 of the tool is pressed into the housing has the adapted form of a socket wrench in order to make the screwing by the tool into the core part 15 by turning the housing 19.

In order to make a soft grip for the operator an extra outside part, for instance a sleeve 27 of a soft material, such as silicon, and having an ergonometrical form is recessed in the front part of the protective housing 19.

While the design of instrument herein described constitutes preferred embodiments of this invention, it is to be understood that the invention is not limited to these precise designs of instrument, and that changes may be made therein without departing from the scope of the invention as defined by the claims.

We claim:

1. A dental device having an exchangeable vibrating working tool, said working tool being rotatably connectable to a movement generating device around which a protective housing is mountable, comprising connecting means for non-rotatably connecting said working tool to said protective housing and for transferring a rotating movement from said protective housing to said working tool to rotatably connect said working tool to said movement generating device.

2. A dental device according to claim 1, wherein said connecting means comprises mating parts having non-circular cross sections comprising the outside of a portion of said working tool insertable into said housing and the inside of a portion of said housing to engage said working tool.

3. Dental device according to claim 1, wherein said connecting means comprises at least one out-cut in a part of said tool insertable into the housing and corresponding, mating, protruding means of the inside of said housing.

4. Dental device according to claim 1, wherein a rear portion of said working tool comprises a threaded portion which is rotatably connectable to said movement generating means.

5. Dental device according to claim 4, wherein said movement generating means comprises an internally threaded portion for receiving said threaded rear portion of said working tool.

6. Dental device according to claim 1, wherein said movement generating device provides ultra sonic vibrations, and said working tool comprises a scalar tip for removing teeth coatings.

7. Dental device according to claim 1, wherein said connecting means comprises mating portions of said working tool and said housing.

8. Dental device according to claim 1, wherein a sealing ring is provided on the working tool and insertable into the front part of the protective housing when the working tool is connected to it.

9. Dental device according to claim 1, wherein the protective housing at its outside comprises a soft part having an ergonometric form adapted to the grip of an operator.

10. Dental device having an exchangeable vibrating working tool, said working tool being rotatably connectable to a movement generating device around which a protective housing is mountable, comprising:

connecting means for non-rotatably connecting said working tool to said protective housing and for transferring a rotating movement from said protective housing to said working tool to rotatably connect said working tool to said movement generating device, wherein said connecting means comprises a groove in said tool at its insertable part, a groove inside said housing opposite to the groove in the tool when the tool is inserted, and an elastic element provided in said grooves.

11. Dental device according to claim 10, wherein said elastic element is an O-ring.

* * * * *